(12) United States Patent
Puls et al.

(10) Patent No.: US 12,213,573 B2
(45) Date of Patent: Feb. 4, 2025

(54) HAIR TREATMENT APPARATUS, HAIR TREATMENT SYSTEM AND METHOD FOR COSMETICALLY TREATING HAIR

(71) Applicant: Henkel AG & Co. KGaA, Duesseldorf (DE)

(72) Inventors: Anna Puls, Winsen (DE); Diane Metten, Hamburg (DE); Katharina Roscher, Hamburg (DE); Thorsten Knappe, Schenefeld (DE); Rolf Bayersdoerfer, Hamburg (DE); Philippe Blank, Kleve (DE)

(73) Assignee: HENKEL AG & CO. KGAA, Duesseldorf (DE)

( * ) Notice: Subject to any disclaimer, the term of this patent is extended or adjusted under 35 U.S.C. 154(b) by 682 days.

(21) Appl. No.: 16/475,568

(22) PCT Filed: Dec. 13, 2017

(86) PCT No.: PCT/EP2017/082654
§ 371 (c)(1),
(2) Date: Jul. 2, 2019

(87) PCT Pub. No.: WO2018/127371
PCT Pub. Date: Jul. 12, 2018

(65) Prior Publication Data
US 2021/0127811 A1    May 6, 2021

(30) Foreign Application Priority Data
Jan. 4, 2017  (DE) ..................... 10 2017 200 073.2

(51) Int. Cl.
*A45D 19/00*  (2006.01)
*A45D 1/04*  (2006.01)
(Continued)

(52) U.S. Cl.
CPC ............... *A45D 1/28* (2013.01); *A45D 1/04* (2013.01); *A45D 2/001* (2013.01); *A45D 20/30* (2013.01);
(Continued)

(58) Field of Classification Search
CPC ...... A45D 2044/007; A45D 1/28; A45D 7/02; A45D 7/06; A45D 20/30; A45D 20/10; A45D 19/16; A45D 2/001
See application file for complete search history.

(56) References Cited

U.S. PATENT DOCUMENTS

2008/0007273 A1* 1/2008 Sherman ................ G01N 22/04
324/640
2012/0312320 A1* 12/2012 Humphreys ............. A45D 1/28
132/211
(Continued)

FOREIGN PATENT DOCUMENTS

EP          1691195 A1    8/2006
FR          3000877 A1    7/2014
WO   WO 2018023117    *    1/2018

OTHER PUBLICATIONS

EPO, International Search Report and Written Opinion issued in International Application No. PCT/EP2017/082654, dated Jan. 26, 2018.

*Primary Examiner* — Rachel R Steitz
*Assistant Examiner* — Brianne E Kalach
(74) *Attorney, Agent, or Firm* — Lorenz & Kopf, LLP

(57) ABSTRACT

In various embodiments, a hair treatment device is provided. The hair treatment device can have a device body, at least one sensor arranged in or on the device body for detecting a hair condition parameter, and an electronic circuit device arranged in or on the device body. The electronic circuit device can be coupled to the at least one sensor for receiving the detected hair condition parameter, and the electronic
(Continued)

circuit device can be configured, based on the received detected hair condition parameter, to control at least one hair treatment parameter and/or to dose at least one hair treatment agent and/or to provide a hair treatment recommendation.

15 Claims, 9 Drawing Sheets

(51) Int. Cl.
*A45D 1/28* (2006.01)
*A45D 2/00* (2006.01)
*A45D 20/30* (2006.01)
*A45D 44/00* (2006.01)

(52) U.S. Cl.
CPC ...... *A45D 44/005* (2013.01); *A45D 2044/007* (2013.01)

(56) References Cited

U.S. PATENT DOCUMENTS

| | | |
|---|---|---|
| 2015/0342515 A1 | 12/2015 | Hutchings et al. |
| 2017/0119130 A1* | 5/2017 | Witchell ................ G01N 21/31 |
| 2018/0075776 A1* | 3/2018 | Heitmann ............ A45D 44/005 |
| 2018/0125207 A1* | 5/2018 | Shami ................... B01F 33/846 |
| 2019/0350346 A1* | 11/2019 | Samain ................ A45D 44/005 |

* cited by examiner

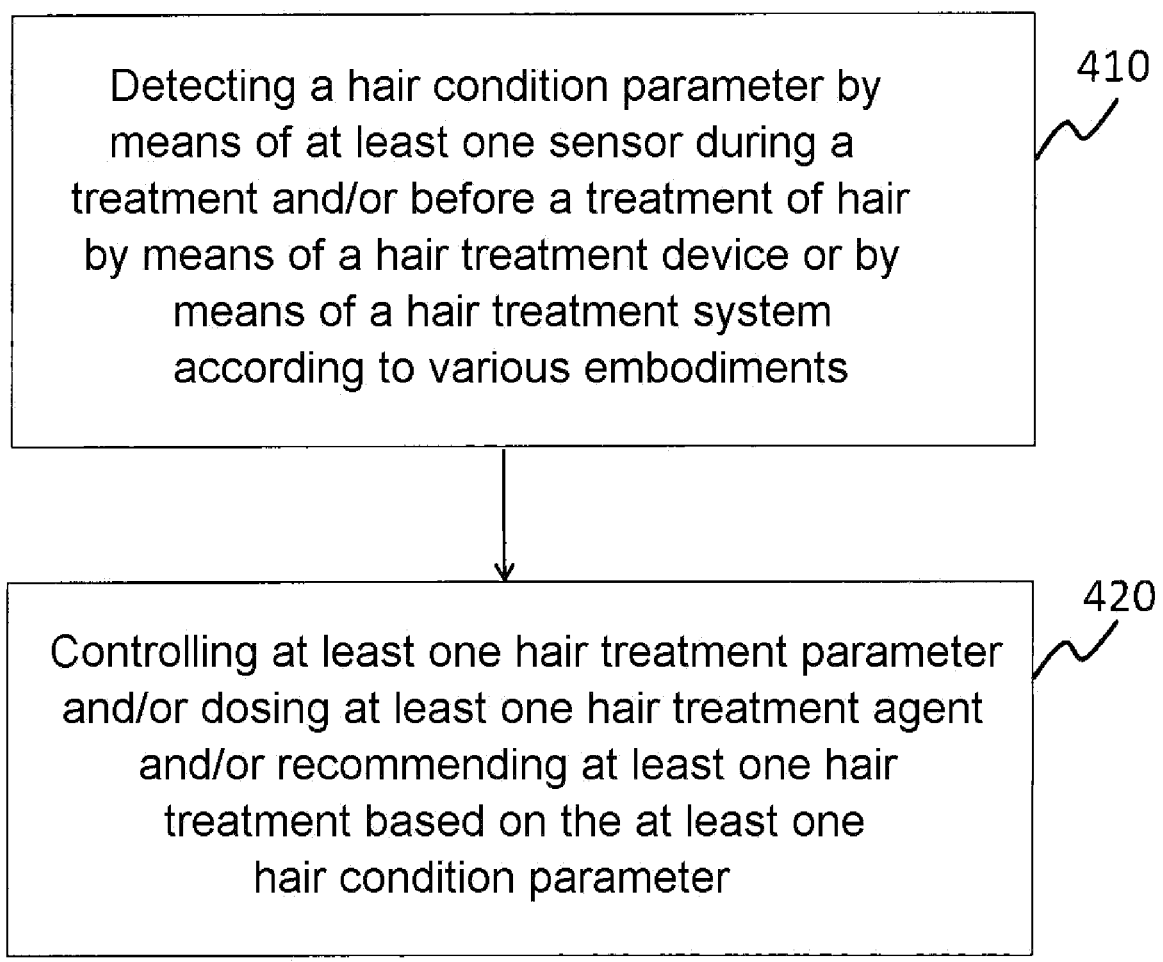

HAIR TREATMENT APPARATUS, HAIR TREATMENT SYSTEM AND METHOD FOR COSMETICALLY TREATING HAIR

CROSS-REFERENCE TO RELATED APPLICATION

This application is a U.S. National-Stage entry under 35 U.S.C. § 371 based on International Application No. PCT/EP2017/082654, filed Dec. 13, 2017, which was published under PCT Article 21(2) and which claims priority to German Application No. 10 2017 200 073.2, filed Jan. 4, 2017, which are all hereby incorporated in their entirety by reference.

TECHNICAL FIELD

The present disclosure relates to hair cosmetics, in particular a hair treatment device, a hair treatment system and a method for the cosmetic treatment of hair.

BACKGROUND

Users (also referred to as consumers) often do not know to what extent their hair is damaged, and often otherwise know little about the condition of their hair. The hair condition, and especially the degree of hair damage, can vary widely depending on the treatment history and make-up. This information can be important in order to be able to select a correct, that is, for the degree of hair damage, suitable cosmetic hair treatment and/or cosmetic hair treatment agent.

Areas of hair cosmetics include, for example, hair styling, hair care, hair shaping (for example, straightening and/or curling, permanent, semi-permanent, or temporary, wherein temporary hair shaping also is considered to be associated with the hair styling area) and/or hair coloration (also referred to as hair coloring, permanent or temporary).

Hair styling and temporary hair deformation can essentially be based on an effect of hair styling agents. In this case, the hair is usually coated on the surface with a styling agent. This coating causes a change of holding properties of the hair.

The styling products should be adapted to the individual condition of the hair or be selected taking into account the individual condition.

Likewise, care products should be adapted to the individual condition of the hair. Users often use improper care products, that is, not suitable for their hair condition, which make the hair heavy or difficult to handle.

In semi-permanent hair deformation, there is intervention in the hair structure to achieve the cosmetic effect. This is done, for example, by heating the hair by employing a straightening iron or a curling iron. This process may not be harmless to the hair due to the high temperatures (from about 120° C. to about 240° C.) that are acting on the hair. In particular, previously damaged hair can be severely (further) damaged in a misapplied semi-permanent hair deformation, for example, when there is too much (further) heat input by a straightening iron.

The exact coordination of the temperatures used in the straightening and/or cosmetic care products can therefore have an even greater significance in the semi-permanent hair deformation than in the care and temporary hair deformation method described above.

With regard to hair coloring, damaged, already dyed and/or gray hair can often lead to deviations from a desired dyeing result in the case of dyeings (for example, for dyeings that the user performs himself).

There is thus a need to provide a user with targeted and individual care instructions in the field of hair care, hair styling, hair coloring and/or hair formation.

Furthermore, the user has a need for simpler and less time-consuming cosmetic methods.

In addition, it would be desirable to enable the user to objectively assess treatment success and/or course of treatment during a cosmetic hair treatment.

SUMMARY

In various embodiments, a hair treatment device is provided which determines a hair condition by at least one integrated sensor and, based on the determined hair condition, controls a hair treatment parameter and/or doses at least one hair treatment agent and/or provides a hair treatment recommendation. In various embodiments, the hair treatment parameter can be a parameter that is adjustable on the hair treatment device, for example, a temperature of the hair treatment device. In various embodiments, the hair treatment agent can be applied by the hair treatment device, for example, on the hair and/or on the scalp, and a dosage, for example, by employing valves, can be carried out by the hair treatment device. In various embodiments, the hair treatment recommendation can refer to hair treatment parameters of a hair treatment made by the hair treatment device that are inaccessible to a direct control by the hair treatment device, for example, a recommendation as to which hair treatment agents to fill in tanks of the hair treatment device and/or at what speed hair treatment must carried out along the hair, or the like.

In various embodiments, a delivery of care and/or styling agents and a heating of the hair can be combined in a method step in a semi-permanent formation of the hair.

Various embodiments provide methods for semi-permanent hair deformation, temporary hair deformation and hair care.

In the field of semi-permanent hair deformation, methods are provided in various embodiments using small power-carrying devices such as straightening irons, curling irons or drying hoods, and the hair treatment devices and hair treatment systems suitable therefor.

In the field of temporary hair deformation and hair care, methods are provided in various embodiments using small power-carrying devices such as combs or brushes, and the hair treatment devices and hair treatment systems suitable therefor.

In various embodiments, methods are provided which use a combination of a styling device (for example, comb, brush, curling iron, drying hood, in particular straightening iron), a sensor, that is, at least one sensor, wherein the at least one sensor can be integrated or not integrated into the styling device, a processor and an actuator.

Further, hair treatment devices and hair treatment systems are provided which have a combination of a styling device (for example, comb, brush, curling iron, drying hood, in particular straightening iron), a sensor, that is, at least one sensor, wherein the at least one sensor can be integrated or not integrated into the styling device, a processor and an actuator.

In various embodiments, the processor can be configured to receive sensor data from the sensor, to evaluate the sensor data and, possibly, to compare the evaluated sensor data with at least one external database (for example, by a cloud).

In various embodiments, the processor can further be configured to derive handling instructions from the evaluated sensor data (for example, a method profile including temperature and/or used care and/or styling agents).

In various embodiments, the processor can be further configured to possible transmit handling instructions to the actuator, wherein the actuator can be part of the hair treatment device or the hair treatment system.

In various embodiments, the actuator can implement the handling instruction provided by the processor. A handling executed by the actuator can have an optical effect in various embodiments (for example, as a warning light, image, diagram, pictogram, on a screen, for example, the screen of a smartphone, film shown, or the like). In various embodiments, the handling executed by the actuator can have a mechanical effect (for example, as automatic temperature adjustment and/or automatic dosing adjustment on the styling device and/or a vibration). In various embodiments, the handling executed by the actuator can have an acoustic effect (for example, as a warning tone, voice output, or the like).

In various embodiments, the sensor can have a hair damage sensor. The hair damage sensor can be configured in various embodiments to determine, by employing near-infrared spectroscopy and/or fluorescence spectroscopy, a content of oxidative and/or chemical degradation products of hair ingredients, in particular a cysteic acid content of the hair and to determine therefrom a degree of hair damage. The hair damage sensor can be configured in various embodiments to record acoustic emissions detected during combing of the hair, and to determine the degree of hair damage of the hair therefrom, possibly with the aid of the processor.

In various embodiments, the hair damage sensor can have a microscopic photosensor. The microscopic photosensor can be configured to detect a hair surface roughness or to enable the determination of hair surface roughness.

In various embodiments, the sensor can have a hair thickness sensor. The hair thickness sensor can be configured in various embodiments to determine a hair thickness by employing a light sensor. For example, when determining the hair thickness, one can consider that thicker hair absorbs more light. In various embodiments, the hair thickness sensor can be configured such that a predetermined amount of hair, for example, single-layer, can be introduced into a given volume and the volume of light is irradiated with a predetermined intensity, wherein the amount of light that reaches the sensor after penetrating the hair can be measured by the sensor. The hair thickness can be determined on the basis of the detected light by the hair thickness sensor, possibly in conjunction with the processor. In various embodiments, the hair thickness sensor, for example, in a case where the hair thickness sensor has a color camera, can also be used for determining a hair color and/or a gray component, possibly with the aid of the processor.

The hair thickness device can have an ultrasound sensor in various embodiments. The ultrasonic sensor can be configured to emit ultrasonic waves in the direction of the hair, to detect ultrasonic waves reflected by the hair and, therefrom, possibly in conjunction with the processor, to determine the hair thickness.

In various embodiments, the at least one sensor can have a hair length sensor. For example, the hair length sensor can have at least one position sensor which makes it possible to determine a distance covered in the hair. In various embodiments, the hair length sensor can be combined with a sensor for calculating combability of the hair (see below).

In various embodiments, the hair length can be provided by the user instead of determining the hair length by the hair length sensor. For example, the user can measure the hair length himself and provide the measured hair length value to the hair treatment device or the hair treatment system.

In various embodiments, the hair thickness sensor can have a photo-optical sensor in which an image of at least one hair is recorded.

In various embodiments, the hair thickness sensor can have a thermal sensor.

In various embodiments, the at least one sensor can have a gray component sensor. From the at least one gray component sensor, an image of the hair can be recorded by employing an optical sensor, for example, by a camera. To determine the gray component in the hair, the image can be compared in various embodiments with at least one existing image, for example, a reference image, which can be stored, for example, internally and/or externally, in order to determine the gray component.

In various embodiments, the sensor can have a straightness/curl sensor that can be configured to determine a hair structure in the sense of straight hair to curly or frizzy hair. The straightness/curl sensor can have a camera in various embodiments. The straightness/curl sensor can be configured in various embodiments, possibly in conjunction with the processor, for example, by employing an image processing program, to determine a straightness or curl of the hair.

In various embodiments, the sensor can have a hair moisture sensor. The hair moisture sensor can be configured in various embodiments to determine a water content of the hair. The hair moisture sensor can, for example, be designed as a near-infrared spectroscope, which can be configured to examine near-infrared (NIR) absorption structures of water and, based on this, possibly with the aid of the processor, to determine the hair moisture.

In various embodiments, the at least one sensor can have a combing work sensor. The combability sensor can be configured to detect a force (for example, by strain gauges), which is used in combing the hair.

In various embodiments, the sensor can have a color sensor. The color sensor can detect the hair color of a user. In various embodiments, the color sensor can comprise or be a high-end multi-band sensor or color sensor with high-bandwidth or a multi-spectral color sensor.

In various embodiments, the at least one sensor can have a hair density sensor. The hair density sensor can have, for example, a camera or a camera attachment which can be configured to be held directly to a region of the hair root, for example, to be placed directly on a scalp. A hair density can be based on the image, for example, based on a number of hairs and/or a distance between the hairs, to determine the hair density.

In various embodiments, the sensor can be configured to determine further hair condition parameters.

In various embodiments, the sensor, for example, in the case of a spectrometer or a camera, can be configured to determine several hair condition parameters, for example, both the degree of hair damage based on the cysteic acid absorption structures in the NIR spectrum and the hair moisture based on the water absorption structures in the NIR spectrum.

In various embodiments, the hair treatment device or the hair treatment system can have or can be a heatable device. That is, in various embodiments, the hair treatment device or the hair treatment system can have a heating device. The heating device can be controlled or regulated in various embodiments depending on the result of the hair analysis (damage, hair thickness, curl, water content). For example, for more intact, thicker, curlier and/or wetter hair, the hair treatment device or hair treatment system can be controlled or regulated to treat the hair at a higher temperature than when the hair is damaged, thinner, straighter and/or drier.

In various embodiments, the hair treatment device and/or the hair treatment system can have a straightening iron, a curling iron and/or a drying hood with a temperature control and/or a temperature regulation.

In various embodiments, the hair treatment device and/or the hair treatment system can have a straightening iron, a curling iron and/or a drying hood with a (for example, refillable) tank for receiving and dosed delivery of a hair treatment agent (also referred to as active substance tank) and a dosing device.

In various embodiments, the hair treatment device and/or the hair treatment system can have a comb and/or a brush with a (for example, refillable) tank for receiving and dosed delivery of a hair treatment agent and a dosing device.

In various embodiments, the hair treatment device and/or the hair treatment system, for example, the styling device, can have the sensors in a double design. In this case, a plurality of (for example, similar) sensors can be arranged such that the user can immediately receive feedback on whether further treatment (also referred to as "post-treatment") is necessary. In various embodiments, the hair treatment device and/or the hair treatment system, for example, the styling device, can have sensors on both sides of the heating device, wherein a sensor measures a hair condition parameter before and a sensor measures a hair condition parameter (for example, the same) after the temperature treatment of the hair.

In various embodiments, the hair treatment device and/or the hair treatment system, for example, the styling device, can alternatively or additionally have a dispensing device. A hair treatment agent, such as a care or styling agent, can be located in the delivery device. Depending on the result of the hair analysis (damage, hair thickness, curl, water content), the hair treatment agent, which can have, for example, a (for example, chemical) composition, optionally in different volumes/amounts depending on the position (hair line, middle, tips), can be applied to the hair.

In various embodiments, by the hair treatment device and/or the hair treatment system, two or more agents in different mixing ratios depending on position (hair line, middle, tips) or at different positions can be applied to the hair.

In various embodiments, the hair treatment device and/or the hair treatment system can have a dispensing device that can have pumps for dispensing the agent, which can be or are controlled, for example, by wireless instructions (for example, instructions transmitted by WLAN, Bluetooth, or the like), which can be sent by the processor. For example, a flow rate of the agent(s) can be adjusted.

In various embodiments, a user can receive information about a condition of his hair (also referred to as hair status).

In various embodiments, a user can receive a personalized cosmetic treatment and/or treatment recommendation adapted to his hair status.

In various embodiments, a user can already receive information about a course of the application while performing a hair treatment. A hair treatment result can still be optimized while performing the hair treatment so that frustration can be avoided.

In various embodiments, a time-saving hair treatment method can be provided, for example, by performing a (temporary, semi-permanent or permanent) hair forming treatment at least in part together with a hair care treatment.

In various embodiments, a hair treatment device can be provided in the form of a straightening iron, in which the at least one sensor is integrated into the straightening iron, an electronic circuit device which can have a processor, is integrated into the straightening iron, and a first actuator which can, for example, have a temperature control or a temperature regulation, which controls or regulates a temperature of heatable surfaces of the straightening iron, is integrated into the straightening iron. In addition, in various embodiments, the straightening iron can have a second actuator, which can have, for example, a doser for a hair care and/or hair styling agent.

In various embodiments, a hair treatment system can be provided in the form of a straightening iron, in which the at least one sensor is part of a first separate communication capable device (for example, having a data exchange device) (for example, a smartphone having a camera, a spectrometer with the data exchange device, or a so-called "acoustic comb" which can be configured to detect noise generated during combing), an electronic circuit device, which can have a processor, is integrated into the straightening iron, and a first actuator which can have, for example, a temperature control or a temperature regulation which controls or regulates a temperature of heatable surfaces of the straightening iron, is integrated into the straightening iron. In addition, in various embodiments, the straightening iron can have a second actuator, which can have, for example, a doser for a hair care and/or hair styling agent. In various embodiments, the straightening iron can have a data exchange device, for example, for receiving measured values detected by the at least one sensor.

In various embodiments, a hair treatment system can be provided in the form of a straightening iron, in which the at least one sensor is part of a first separate communication capable device (for example, having a data exchange device) (for example, a smartphone having a camera, a spectrometer with the data exchange device, or a so-called "acoustic comb" which can be configured to detect noise generated during combing), an electronic circuit device, which can have a processor, is integrated into the first separate communication capable device, and a first actuator which can have, for example, a temperature control or a temperature regulation which controls or regulates a temperature of heatable surfaces of the straightening iron, is integrated into the straightening iron. In addition, in various embodiments, the straightening iron can have a second actuator, which can have, for example, a doser for a hair care and/or hair styling agent. In various embodiments, the straightening iron can have a data exchange device, for example, for receiving recommendations and/or control instructions determined by the electronic circuit device.

In various embodiments, a hair treatment system can be provided in the form of a straightening iron, in which the at least one sensor in which the at least one sensor is integrated into the straightening iron, an electronic circuit device, that can have a processor, is part of a second separate communication capable (that is, having a data exchange device) (for example, part of a smartphone on which, for example, an app can be installed, or for example, a cloud or the like), and a first actuator, which can for example, have a temperature control or a temperature regulation, which controls or regulates a temperature of heatable surfaces of the straightening iron, is integrated into the straightening iron. In addition, in various embodiments, the straightening iron can have a second actuator, which can have, for example, a doser for a hair care and/or hair styling agent. In various embodiments, the straightening iron can have a data exchange device, for example, for receiving recommendations and/or control instructions determined by the electronic circuit device.

In various embodiments, a hair treatment system can be provided in the form of a straightening iron, in which the at least one sensor is part of a first separate communication capable device (for example, having a data exchange device) (for example, a smartphone having a camera, a spectrometer with the data exchange device, or a so-called "acoustic comb" which can be configured to determine noise generated during combing), an electronic circuit device, that can have a processor, is part of a second separate communication capable device (for example, having a data exchange device) (for example, part of a smartphone on which, for example, an app can be installed, or for example, a cloud or the like), and a first actuator, which can have, for example, a temperature control or a temperature regulation which can control or regulate a temperature of heatable surfaces of the straightening iron, is integrated into the straightening iron. In addition, in various embodiments, the straightening iron can have a second actuator, which can have, for example, a doser for a hair care and/or hair styling agent. In various embodiments, the straightening iron can have a data exchange device, for example, for receiving recommendations and/or control instructions determined by the electronic circuit device.

In various embodiments, a hair treatment device can be provided in the form of a comb, in which the at least one sensor (for example, in the form of a microphone or a camera for detecting hair condition parameters) is integrated into the comb, an electronic circuit device, which can have a processor, is integrated into the comb, wherein the processor can be configured to determine by the detected hair condition parameters, for example, a degree of hair damage and based thereon, to determine at least one control parameter and possibly at least one recommendation, and a first actuator which can, for example, have a doser for a hair care and/or hair styling agent, is integrated into the comb or is connectable to the comb to an integrated system, for example, in the form of an attachment for the comb.

In various embodiments, a hair treatment system can be provided in the form of a comb, in which the at least one sensor is part of a first separate communication capable device (for example, having a data exchange device) (for example, a smartphone having a camera, a spectrometer with the data exchange device, or a so-called "acoustic comb"), an electronic circuit device, which can have a processor, is integrated into the comb, wherein the processor can be configured to determine, by the detected hair condition parameters, for example, a degree of hair damage and based thereon, to determine at least one control parameter and possibly at least one recommendation, and a first actuator, which can have, for example, a doser for a hair care and/or hair styling agent, is integrated into the comb or is connectable to the comb to an integrated system, for example, in the form of an attachment for the comb. In various embodiments, the comb can have a data exchange device, for example, for receiving recommendations and/or control instructions determined by the electronic circuit device.

In various embodiments, a hair treatment system can be provided in the form of a comb, in which the at least one sensor is part of a first separate communication capable device (for example, having a data exchange device) (for example, a smartphone having a camera, a spectrometer with the data exchange device, or a so-called "acoustic comb"), an electronic circuit device, that can have a processor, is integrated into the first separate communication capable device, and a first actuator, which can have, for example, a doser for a hair care and/or hair styling agent, is integrated into the comb or is connectable to the comb to an integrated system, for example, in the form of an attachment for the comb. In various embodiments, the comb can have a data exchange device, for example, for receiving recommendations and/or control instructions determined by the electronic circuit device.

In various embodiments, a hair treatment system can be provided in the form of a comb, in which the at least one sensor is integrated into the comb, an electronic circuit device, that can have a processor, is part of a second separate communication capable device (that is, having a data exchange device) (for example, part of a smartphone, on which an app can be installed, or for example, a cloud or the like), and a first actuator, which can, for example, have a doser for a hair care and/or hair styling agent, is integrated into the comb or is connectable to the comb to an integrated system, for example, in the form of an attachment for the comb. In various embodiments, the comb can have a data exchange device, for example, for receiving recommendations and/or control instructions determined by the electronic circuit device.

In various embodiments, a hair treatment system can be provided in the form of a comb, in which the at least one sensor is part of a first separate communication capable device (for example, having a data exchange device) (for example, a smartphone having a camera, a spectrometer with the data exchange device, a so-called "acoustic comb"), an electronic circuit device, which can have a processor, is part of a second separate communication capable device (that is, having a data exchange device) (for example, part of a smartphone on which, for example, an app can be installed, or for example, a cloud or the like), and a first actuator, which can, for example, have a doser for a hair care and/or hair styling agent, is integrated into the comb or is connectable to the comb to an integrated system, for example, in the form of an attachment for the comb. In various embodiments, the comb can have a data exchange device, for example, for receiving recommendations and/or control instructions determined by the electronic circuit device.

In various embodiments, a hair treatment system can be provided, which can have a hair treatment device (for example, a straightening iron, a curling iron, a comb, a brush, or the like), and further, a hair condition determination device which can be configured to detect a degree of hair damage, for example, by employing at least one sensor integrated into the hair condition determination device (the hair condition detection device can, for example, have a comb equipped with sensors or an NIR camera or an NIR spectrometer or a UV spectrometer or a UV/VIS spectrometer or a VIS/NIR spectrometer, which can be suitable for determining a hair condition parameter, for example, a hair structure). Via a smartphone app that can act as the heart of the system, targeted information, such as control or regulation instructions, can be then transmitted to the hair treatment device (for example, a "smart" straightening iron), which can be configured, based on the control or regulation instructions, to control or regulate a hair treatment parameter and/or to dose a hair treatment agent (in the case of the straightening iron, for example, a temperature can be adjusted, with which the hair can be treated without further damage). A data exchange can be made wirelessly, for example, via Bluetooth, WLAN or near field communication technology (NFC technology).

In various embodiments, a hair treatment system can be provided, which can have a hair treatment device (for example, a straightening iron, a curling iron, a comb, a brush, or the like), and further can have a data connection (the term connectivity is also used for the option of data exchange) between an external app and the hair treatment device (for example, a hair care/styling device). In various embodiments, care/styling parameters can be provided, for example, predetermined (in a case where the hair treatment device has the straightening iron or curling iron, the parameter can, for example, have a maximum temperature), wherein the parameter provided can be related to a degree of damage of the hair, that is, depending on the degree of damage of the hair, the parameter can have a different value.

In various embodiments, a temperature of a straightening iron can be controlled or regulated, taking into account a degree of damage of the hair.

In various embodiments, a "smart" styling device (for example, a comb, a brush, a curling iron, a straightening iron, or the like) and/or a "smart" terminal (for example, a smartphone, a tablet, a smart mirror, or the like) can have a sensor which can be integrated into the styling device and/or the terminal and/or designed as a removable attachment and/or as a separate portable device. The styling device and/or the terminal can be configured to detect one or more hair condition parameters, for example, hair characteristics. The detected data can be evaluated by the styling device and/or the terminal, for example, by employing an app and/or a program which can be installed on the styling device and/or the terminal, and a (personalized) recommendation can be provided to the user, for example, in the form of so-called DOs (recommendations) and DON'Ts (warnings). An example of this would be "Take or do not take a waxy product". In various embodiments, the providing of the recommendation can be made optically, for example, by employing a display device, for example, by a display. In various embodiments, the providing of the recommendation can alternatively or additionally be made acoustically, for example, as a voice output. In various embodiments, the providing of the recommendation can be made by the styling device and/or by the terminal.

In various embodiments, the hair treatment device or the hair treatment system can have an input device. The input device can be configured to receive at least one input by the user and to provide it to the electronic circuit device and/or an external data processing device. Parameters to be input by the user can have, for example, a desired hair color, a desired treatment (for example, hair formation, styling, care), a hair length, a hair curl (for example, comparative images can be provided for an input) or the like.

In various embodiments, the hair treatment device, for example, the smart styling device, can further have a dispensing device. For example, a hair treatment agent can be arranged in at least one tank in the dispensing device in various embodiments, for example, a hair care agent, a hair styling agent or a hair coloring agent. In various embodiments, depending on the determined at least one hair condition parameter (which can be a result of a hair analysis performed based on the sensor data), the hair treatment agent can be applied in different volumes or amounts depending on the position (for example, hair line/middle/tips), for example, a different volume/amount on the hair tips than on the hairline. Alternatively or additionally, two or more hair treatment compositions in different mixing ratios can be applied to the hair, depending on the position (for example, hairline/middle/tips) or at different hair sites (for example, as an ombre coloring). The dispensing device can have at least one pump for dispensing the hair treatment agent. The at least one pump can be controlled or regulated, for example, by employing a smartphone or the like, for example, by an app. For example, a flow rate of the hair treatment agent can be adjusted by the smartphone.

In various embodiments, the dispensing device can be separate from the hair treatment device.

The dispensing device can, in various embodiments, be controlled by employing a wireless transmission device, for example, by the dispensing device receiving control commands be the wireless transmission device. The wireless transmission device can be part of the electronic circuit device, for example. The wireless transmission device can, in various embodiments, have a chip or tag which enables the wireless data transmission, for example, by Bluetooth, WLAN (WiFi), Zigbee, NFC, Wibree, Thread, WiMAX or the like.

In various embodiments, providing the recommendation to the user can include providing by transmitting the recommendation to a display device and displaying the recommendation.

The transmission can be done in various embodiments by employing a wireless transmission device. The wireless transmission device can be part of the electronic circuit device, for example. The wireless transmission device can, in various embodiments, have a chip or tag which enables the wireless data transmission, for example, by Bluetooth, WLAN (WiFi), Zigbee, NFC, Wibree, Thread, WiMAX or the like.

In various embodiments, prior to providing a recommendation to the user, a data comparison can be made between the smart terminal and/or the smart styling device and data, for example, reference data, which can be stored, for example, in a cloud. In various embodiments, the data can have data from other users having, for example, the same at least one hair condition parameter, and, for example, corresponding derived recommendations/measures.

In various embodiments, a user can already receive information about a course of the application while performing a hair treatment. This can make it possible to already optimize a hair treatment result during the performance. This can avoid frustration for the user.

In various embodiments, a user can obtain information about a hair condition, that is, a status of the hair, which enables (for example, direct) instructions to be generated, for example, an instruction as to when a dyeing process must be finished (for example, by timely rinsing of the hair, to avoid a dark dyeing result).

In various embodiments, the recommendation for care and styling products and/or the use instructions can refer to a chemical composition of the recommended and not recommended care, and styling products, for example, in the form of so-called DOs (recommendations) and DON'Ts (warnings). An example of this would be "Take or do not take a waxy product".

Depending on the hair thickness and hair density, the user can be given a recommendation on a suitable styling product in various embodiments. For example, it can be disadvantageous to use a styling wax on thin, light hair, as this will quickly cause greasiness and unkemptness in such a hair type. The category "wax" includes products which are distinguished by a high proportion of wax components, vaselines, emulsifiers and oils or oily or oil-containing components. Also not recommended for thin light hair can be emulsions, which can also be exemplified by a high proportion of just described raw materials.

Depending on the nature of the ingredients used in the hair care and/or hair styling products, the use of these ingredients in a determined hair type can be recommended to the user or can be discouraged from use.

Depending on the curl condition (curls or rather waves), the user can be advised, in various embodiments, that a product either supports his natural curl image, or in the case of waves also strengthens (also known as pushing) and stabilizes. Certain polymers, such as Styleze CC10 (VP/DMAPA Acrylates Copolymer), Mirustyle CP (Polyquaternium-72), can be particularly helpful here. However, standard polymers, such as PVP, PVP/VA, etc. can well be suitable for holding the curls, and/or further polymers whose curl-holding or generation properties are known to those skilled in the art at the time of publication.

Curls usually require a lot of care, so that even with curly hair, a nourishing emulsion/lotion can be beneficial. Furthermore mousses can be applied to support bounce and springiness and to define the curls. In various embodiments, the polymers mentioned above for curl definition can be used. The curl definition can also be achieved with a light wax, whereas a (heavy) wax acts more as a drag on waves and probably can not help the consumer to maintain his styling result over a longer time period. However, in various embodiments, additional support can also be provided here by polymers (for example, as mentioned above) in order to prolong the result and the holding power.

Even with long hair, an application of a wax or gel can be unusual in various embodiments. In this case, the user can be advised to fall back to lighter consistencies, such as blow-dry sprays, mousses, lotions or the like, in order to support their look. Particularly sprayable or low-viscosity pumpable products can be well suited here, since they can be distributed particularly easily over the entire hair length. Depending on the desired styling effect, there can also be polymer types that can be used (for example, PVP, PVP/VA, Chitosan, Polyquaternium types, etc.).

In various embodiments, a choice of the right product can usually be related to the desired styling result. Thus, for example, a blow-dry spray or a mousse can be provided to aid in blow-drying, and can also contain nourishing styling components that allow working with comb and brush in wet hair (for example, Polyquaternium-4,11,46, etc., Chitosan, Polyacrylamidopropyltrimonium Chlorides, etc.).

A hairspray can be provided to fix the final hairstyle and also to protect against external influences endangering the hairstyle. An example of such an external influence would be the influence of high air humidity. Certain polymers can counteract this, for example, amphomer.

Short, strong hair can be well shaped and kept in shape with gels, waxes, pastes, creams and hair sprays.

The longer the hair, the stronger the desire of the user to remove the styling product from the hair before going to bed. Short hair which has been styled with waxes, pastes, creams, gels or the like can usually wash out quickly with water and dry quickly afterwards (possibly by using a hair dryer). Longer hair styled with a styling mousse and/or fixed with a hairspray is often brushed off. For this purpose, it can be helpful when the applied fixing polymer is easily brittle and fragile and can be removed, for example, by using a comb/a brush. Said polymers would be, for example, PVP, PVP/VA, amphomer, etc.

Users with African-American hair can prefer products that have one thing in common: much care. This target group can feel that their hair is very dry and brittle and needs much moisture. In particular, rich, creamy textures can be desirable here, and also oil sprays that make the hairstyle of the user look healthy and well-groomed. Conditioning polymers can help keep the hair in shape without making it stiff and inflexible. Rich waxes and emulsions can provide additional care to the hair and can easily weigh down the hair, so that the hair does not fly (anti-frizz). What would thus be a "no go" on European hair, can not be nurturing/weighing/greasy enough for African-American hair.

Users with damaged, for example, bleached, hair can need more care in their products than people with healthy ("virgin") hair.

In various embodiments, in addition to the chemical properties or instead physical properties of the recommended and not recommended care and styling products (DOs and DON'Ts, for example, viscosities, evaporation properties, stickiness) can be crucial or influential as to whether a product is considered as recommended or not for a given hair type.

The longer the hair, the lower the stickiness of formulations should be. Users with long hair especially often want a styling product that holds and styles, but does not stick very hard. Many of them can prefer a natural hair feel and appearance.

In addition to mousses and light sprays or emulsions for blow-drying, long-haired women can often use hairspray to fix their hairstyle. Again, a non-strong adhesive product can be preferred. In addition, however, it can be desirable for the hairspray to be finely dispersed on the hair to avoid the said effect (a concreted/unnatural looking hairstyle).

Even users with curls can care about supporting the curls and making them look natural, and not cement their look. The thicker and shorter the hair, the higher the product viscosity can be, since it often helps to shape the hair when styling. Here, as already described above, pastes, creams, gels with a high viscosity are suitable.

In various embodiments, in addition to the chemical properties and/or the physical properties, a making-up (also referred to as application form, etc.) of the recommended and not recommended care and styling products (DOs and DON'Ts, for example, spray rather than gel) can be decisive or influential on whether or not a product is considered to be recommended for a given hair type. This is partly described above.

In various embodiments, the determined recommendation can be used to make an optimal/personalized styling product, for example, as an order to make an optimal/personalized styling product.

This can be initiated, for example, by calling a manufacturer's website for optimal/personalized hair treatment products, such as styling products.

The optimal/personalized hair treatment product can be a product specially made for the customer or a so-called mass customized product. In the case of a "mass customized" product, an individualization can be achieved by varying a few characteristics of a product that are decisive from the customer's point of view. Preferably, these "mass customized" products are based on the concept of modularization, that is, the product can be assembled individually from various modules/building blocks.

Often, there are many dependencies between the many different features/ingredients of a product, which can be expressed as "commandments" or "prohibitions." In order to obtain a clear product definition, it can be advantageous for the ordering process to proceed with the aid of a product configurator. This configurator helps the customer to select the characteristics/ingredients and draws attention to the permitted/inadmissible combinations of features, wherein the latter then can not be selected.

With the help of a product configurator, for example, the selection of chemically and/or physically incompatible ingredients or the selection of the ingredients unsuitable for the determined hair condition can be avoided. Conversely, the selection of suitable ingredients for the determined hair condition can be predetermined or suggested by the product configurator.

In various alternative embodiments, a user input can be utilized on a delivery device for the optimized delivery of hair treatment product. This delivery device can preferably be present at a hairdresser or at a point of sale (POS) of hair treatment agents. The user can select his hair condition and, possibly, the desired amount of product using a digital display and a touchscreen. For this purpose, a stored recommendation can already be programmed in the device, for example, stored in a database. Such recommendations can be known from leaflets of hair colorations, on which it can frequently be noted that, for example, two coloration packages should be used for shoulder-length hair. A (quantity and) product recommendation can be made by a previous individual input of the hair length of the user. This can either be confirmed, extended or reduced by the user when, for example, he already knows that he tends to use more/less product than is normally stated on packaging.

In various embodiments, a method for the cosmetic treatment of hair is provided which allows a correct, that is, suitable for the degree of hair damage, product selection. For example, in the hair treatment, an exact matching product can be used for hair coloring, bleaching, perming, hair care and/or hair styling given its degree of hair damage.

In various embodiments, a user can himself determine his degree of hair damage and/or other hair condition parameters for a corresponding evaluation, for example, without performing elaborate microscopy and/or having background knowledge. Thus, the user can be enabled to dispense with expert assistance in determining his hair condition.

Herein, reference can be made to "the sensors", for example, regarding data transmission between the sensors and a data processing device, an arrangement of sensors, etc. It is to be understood that the sensors can have a totality of sensors arranged in the hair treatment device or the hair treatment system, for example, a totality of camera(s), temperature sensor(s), microphone(s), etc., or, if this is evident from the context, a part of said sensors.

In various embodiments, the hair treatment system can have an electronic device, for example, a mobile electronic device (also referred to as a mobile device), for example, a smartphone or a tablet, or for example, another data processing device (for example, a PC). In various embodiments, the hair treatment system can also use an (optionally further) external data processing device, for example, a cloud, for signal evaluation, for example, as an extension of the signal evaluation. For this purpose, in various embodiments, the signals detected by the sensors can be compared with signals stored in a database (also referred to as comparison signals, comparison data, reference signals or reference data). In various embodiments, the degree of hair damage or another hair condition parameter can be classified based on this, for example, by assigning degrees of hair damage to the comparison signals, and assigning the degree of hair damage or the other hair condition parameters of the comparison signal most similar to the measured signal to the measured hair.

In various embodiments, the reference data, which can, for example, be provided as a database, can be obtained empirically (for example, in the laboratory) for hair whose degree of hair damage degree can be known. In various embodiments, further information about the hair can be present, which serves as a basis for the reference spectra, for example, "hair bleached four times—high degree of damage" or "untreated hair—no damage", and/or for the hair which is used to determine the reference spectra, a development of a hair condition, for example, the degree of hair damage can be provided, for example, several reference spectra, each of which was taken after a different hair treatment step, wherein the hair treatment can have a nourishing hair treatment and/or a damaging hair treatment. An agent (for example, product and/or ingredient) used in a treatment can also be detected by the database.

In various embodiments, a user can also be provided with the additional information (for example, the database), for example, which degree of treatment corresponds to his hair condition, and/or how his hair condition is likely to develop when he performs a particular treatment, for example, applies a particular agent.

In various embodiments, for example, when using a cloud, the database can alternatively be generated (for example, continuously supplemented) in the laboratory by employing user data. In various embodiments, the database generated in the laboratory can be supplemented by employing user data which can be provided by the cloud.

In various embodiments, the hair treatment device can be provided as an accessory, for example, a "smart accessory" for a smartphone (or similar device such as a tablet, an iPod, or the like), which can be connected to the smartphone, for example, plugged therein, whereby processing capabilities and/or sensors of the smartphone can be enabled. In various embodiments, the hair treatment system can have such an accessory.

In various embodiments, the hair treatment system can be provided as a stand-alone device, which can have, for example, its own device for transmitting data and thus can be a so-called "Internet of Things (IoT)" device. The stand-alone hair treatment device can transmit the recorded data (for example, acoustic data and possibly speed data) to an external data processing device, for example, to a cloud, for example, by Bluetooth, WLAN (WiFi), NFC or the like.

In various embodiments, the recorded data, as described elsewhere herein, can be analyzed by software algorithms to determine a hair conditional parameter, for example, a degree of hair damage.

In various embodiments, for example, when the reference data are provided by the cloud, these can be available to a user at any time in order to be used as reference data for a comparison.

In various embodiments, the data detected by the hair treatment device or by the hair treatment system can be stored, for example, in a memory integrated into the hair treatment device and/or into the external data processing device, for example, the cloud. The stored data can be stored so that at least the user is enabled to recognize this data as his data. This makes it possible to compare hair information obtained, for example, at different points in time (for example, before and after a treatment) with each other.

In various embodiments, the hair treatment device and/or the hair treatment system can have a connection for transmitting data, for example, between a smartphone/tablet, which can be part of the hair treatment system, and a cloud, and/or between the hair treatment device and a smartphone/tablet, and/or between a hair treatment device and a cloud.

In various embodiments, a known data transmission standard can be used for the data transmission, for example, Bluetooth, WLAN (WiFi), NFC or the like. In various embodiments, the hair treatment device or the hair treatment system can have a corresponding data transmission device for transmitting and/or receiving the data.

In various embodiments, data collected by the hair treatment device (that is, the determined at least one sensor value and/or based on data and/or recommendations and/or a control or regulation parameter determined thereon) can be provided.

In various embodiments, the analysis can be performed by the hair treatment device itself, for example, by the circuit device, and an analysis result can be transmitted to a display device, for example, a display, a speaker, a smartphone, or the like, to provide the analysis result.

In various embodiments, the data can be transmitted to/on an external data processing device (also referred to as an external platform), for example, on a smartphone with app, on a cloud, etc. After the data transmission to the external data processing device, the examination of the data can be executed by this, for example, to determine a control and/or regulation parameter and/or a recommendation.

In various embodiments, a matching of the cosmetic treatment with individualized consumer data can facilitate an iterative cosmetic treatment cycle, improve an outcome of the cosmetic treatment, and/or increase a user's motivation to continue the treatment.

In various embodiments, a user can be provided with information about a status of the hair (also referred to as a hair condition) which can further be used to determine an individual control or regulation of the hair treatment device and/or recommendation adapted to the hair condition of the user, for example, a product recommendation (for example, for a hair care and/or a hair styling product and/or a hair dyeing product) and/or a care recommendation, for example, a care recommendation, which concerns the hair of the user.

In various embodiments, a hair dyeing product can be excluded from the hair treatment agents to be used.

In various embodiments, the control or regulation parameter or the recommendation can be determined directly by the hair treatment device, that is, the electronic circuit device can be configured to determine the control/regulation parameter or the recommendation itself (also referred to as direct). For example, the electronic circuit device can be or have a data processing device, for example, it can be equipped with a memory and a processor, for example, a microprocessor, which can be configured, for example, by programming, to receive the sensor data and either provide it directly to the user, or to use the sensor data to provide the recommendation. For example, the sensor data can be compared with a database, which can have been obtained empirically, for example. Recommendations can be assigned to a plurality of sensor data in the database.

In various embodiments, the electronic circuit device can be configured to indirectly determine the control or regulation parameter of the recommendation, for example, product or treatment recommendation. For example, the electronic circuit device (for example, in addition to a memory and a processor, for example, a microprocessor) can be equipped with a data transfer device which can be configured to transmit the sensor data received by the electronic circuit device to an external data processing device, for example, a computer, for example, a cloud, by which, for example, as described above for determining the control or regulation parameter or the recommendation by the electronic circuit device, the control or regulation parameter or the recommendation can be determined in order to provide the control or regulation parameter or the recommendation, for example, by transmitting to a display device and/or by transmitting the recommendation back to the electronic circuit device (for example, by the data transmission device). In various embodiments, the data transmission can take place in several stages, for example, by first transmitting the sensor data from the circuit device to the display device (for example, a smartphone, a tablet or the like), and the display device transmits the sensor data to the external data processing device (for example, the cloud).

In various embodiments, providing the control or regulation parameter or recommendation can have an adjusting of control or regulation parameters in the device to be controlled or regulated (for example, heatable part of the device, pump of a dispensing device, or the like), and/or a providing by transmitting the recommendation to a display device and displaying the recommendation.

The transmission can be done in various embodiments by employing a wireless transmission device. The wireless transmission device can be part of the electronic circuit device, for example. The wireless transmission device can, in various embodiments, have a chip or tag which enables the wireless data transmission, for example, by Bluetooth, WLAN (WiFi), Zigbee, NFC, Wibree, Thread, WiMAX or the like.

In various embodiments, the display device can have a computer screen, a smartphone, a tablet, an iPad, a smart mirror, a smartwatch, a laptop, or the like.

In various embodiments, a hair treatment device is provided. The hair treatment device can have a device body, at least one sensor arranged in or on the device body for detecting a hair condition parameter, and an electronic circuit device arranged in or on the device body, wherein the electronic circuit device can be coupled to the at least one sensor for receiving the detected hair condition parameter, and wherein the electronic circuit device can be further configured, based on the received detected hair condition parameter, to control at least one hair treatment parameter and/or to dose at least one hair treatment agent and/or to provide a hair treatment recommendation.

The hair treatment device can have a hair straightening iron in various embodiments.

In various embodiments, the controlled hair treatment parameter can have a temperature of the hair treatment device.

In various embodiments, the at least one sensor can be configured to be brought into contact with the hair of the user during the detection of the at least one hair condition parameter.

In various embodiments, the electronic circuit device can be further configured to determine a hair condition information item and/or a recommendation based on the received sensor value and to provide it to the user.

In various embodiments, the recommendation can have at least one recommendation selected from the group including hair care product recommendations, hair styling product recommendations and hair treatment recommendation.

In various embodiments, the at least one sensor can be arranged sealed in the device body.

In various embodiments, the electronic circuit device can have a wireless data exchange device.

In various embodiments, the sensor can have at least one sensor selected from a group of sensors, the group of sensors having: a camera for recording a digital image of the hair, a temperature sensor, a moisture sensor, a microphone, a color sensor and a tensile force gauge.

In various embodiments, a hair treatment system is provided. The hair treatment system can have a hair treatment device according to various embodiments and a display device, wherein the at least one hair treatment device can be configured to transmit to the display device the hair condition information item and/or the recommendation by the data exchange device.

In various embodiments, the display device can have a computer screen, a smartphone, a tablet, an iPad, a smart mirror, a smartwatch or a laptop.

In various embodiments, a hair treatment system is provided. The hair treatment system can have a device body, at least one sensor arranged in or on the device body for detecting a hair condition parameter, an electronic circuit device having a wireless data exchange device and a data processing device arranged in or on the device body, wherein the electronic circuit device can be coupled to the at least one sensor for receiving the detected electronic hair condition parameter, wherein the electronic circuit device can further be configured to transmit the received hair condition parameter to the data processing device by the wireless data exchange device, wherein the data processing device can be configured, based on the received detected hair condition parameter, to determine a control of a hair treatment parameter, and/or a dosage of a hair treatment agent and to transmit to the electronic circuit device or a further electronic circuit device arranged in a treatment device by the wireless data exchange device, and wherein the electronic circuit device or the further electronic circuit device can further be configured to control the at least one hair treatment parameter and/or to dose the at least one hair treatment agent.

In various embodiments, the data processing device can have a smartphone, an iPad or a tablet.

In various embodiments, a method of providing cosmetic treatment of hair of the user is provided. The method can have, during a treatment and/or before a treatment of the hair by a hair treatment device according to various embodiments or by a hair treatment system according to various embodiments, detecting a hair condition parameter by the at least one sensor and controlling at least one hair treatment parameter and/or dosing at least one hair treatment agent and/or recommending at least one hair treatment based on the at least one hair condition parameter.

In various embodiments, the hair treatment parameter can have a temperature of the hair treatment device.

The hair treatment device can have a hair straightening iron in various embodiments.

In various embodiments, the method can further have transmitting the detected hair condition parameter to the data processing device, and receiving the information provided by the external data processing device, wherein the determination of the at least one hair treatment parameter and/or the hair treatment agent dosage can be made based on the at least one hair condition parameter by the data processing device.

BRIEF DESCRIPTION OF THE DRAWINGS

The present disclosure will hereinafter be described in conjunction with the following drawing figures, wherein like numerals denote like elements, and:

FIG. 4 is a flow chart of a method of providing hair condition information according to various embodiments.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

In the following detailed description, reference is made to the accompanying drawings which form a part of the present disclosure and in which is shown by way of illustration specific embodiments in which the present disclosure can be practiced. In this regard, directional terminology such as "top", "bottom", "front", "back", "front", "rear", etc. is used with reference to the orientation of the described figure(s). Since components of embodiments can be positioned in a number of different orientations, the directional terminology is illustrative and is in no way limiting. It should be understood that other embodiments can be utilized and structural or logical changes can be made without departing from the scope of the present disclosure. It should be understood that the features of the various embodiments described herein can be combined with each other unless specifically stated otherwise. The following detailed description is therefore not to be taken in a limiting sense, and the scope of the present disclosure is defined by the appended claims.

Figure 1:
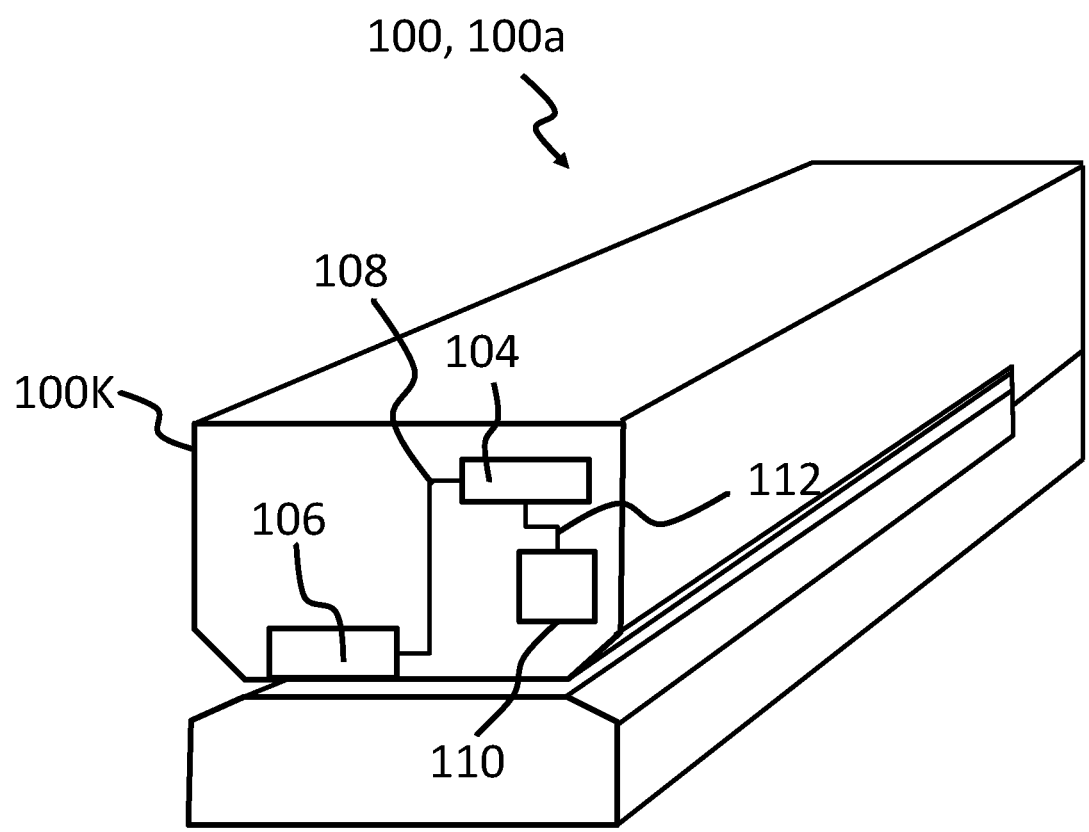
FIG. 1 is a schematic representation of a hair treatment system according to various embodiments.
Figure 2A:
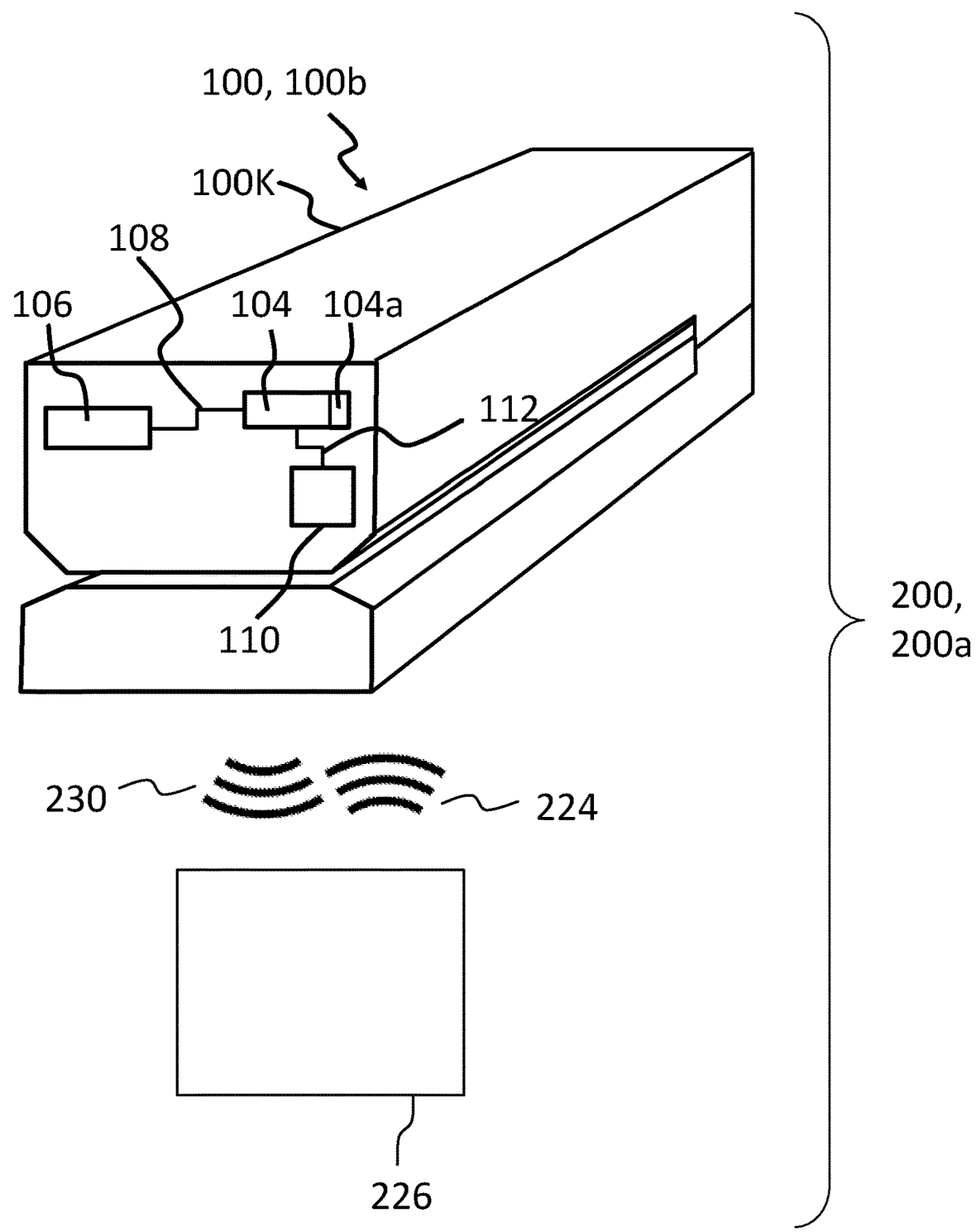
FIGS. 2A to 2E are each a schematic representation of a hair treatment system according to various embodiments.
Figure 2B:
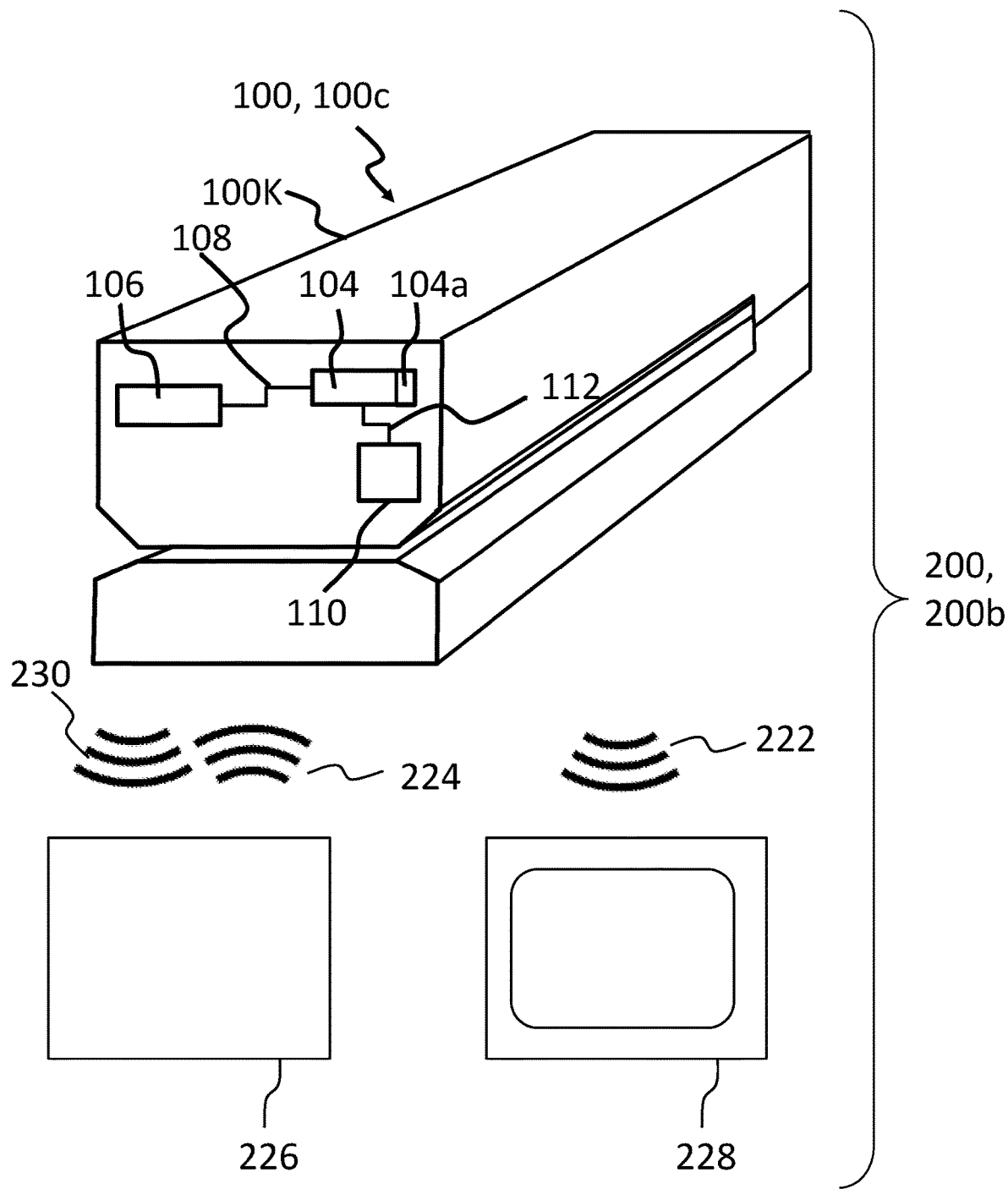
Figure 2C:
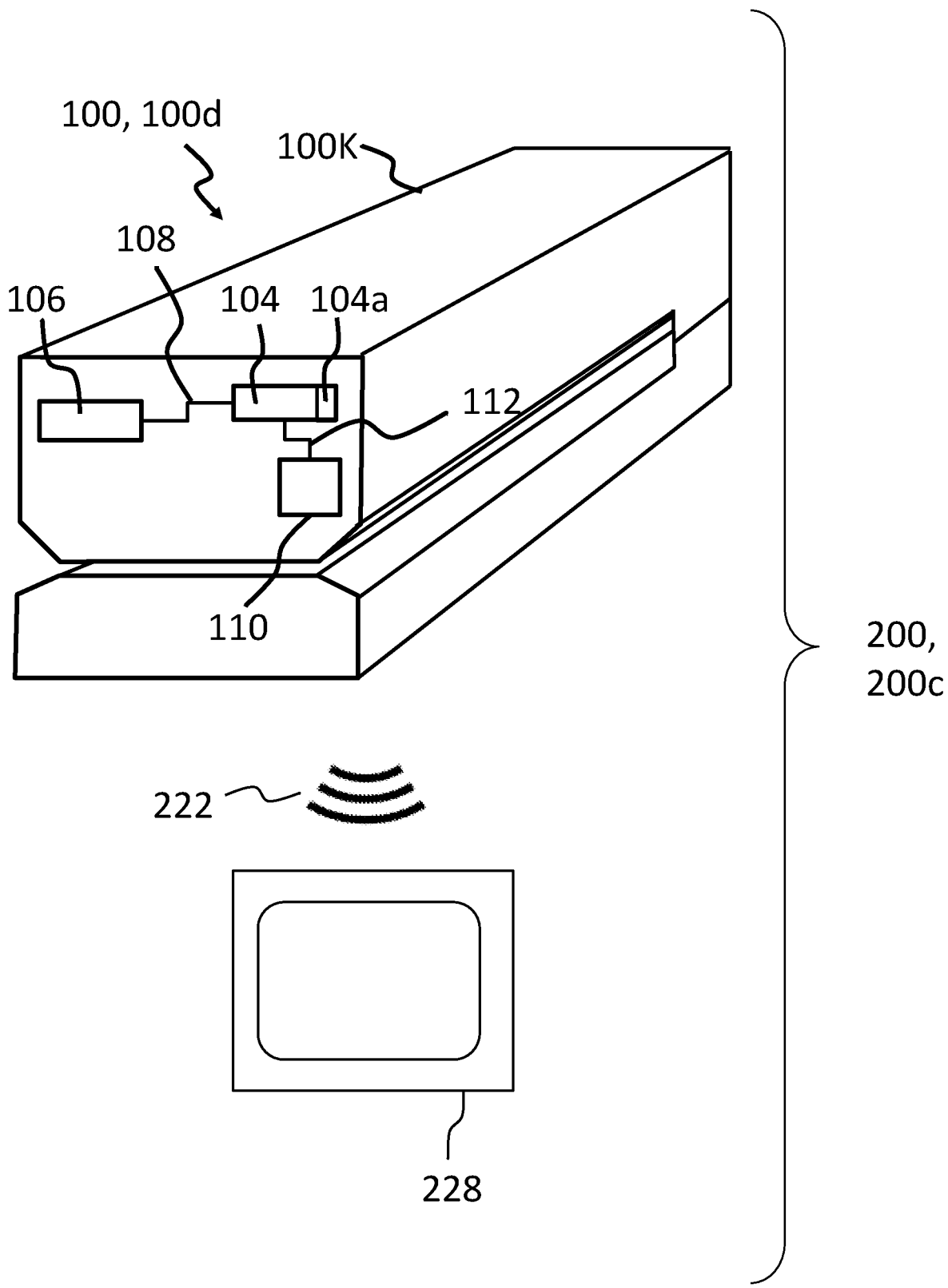
Figure 2D:
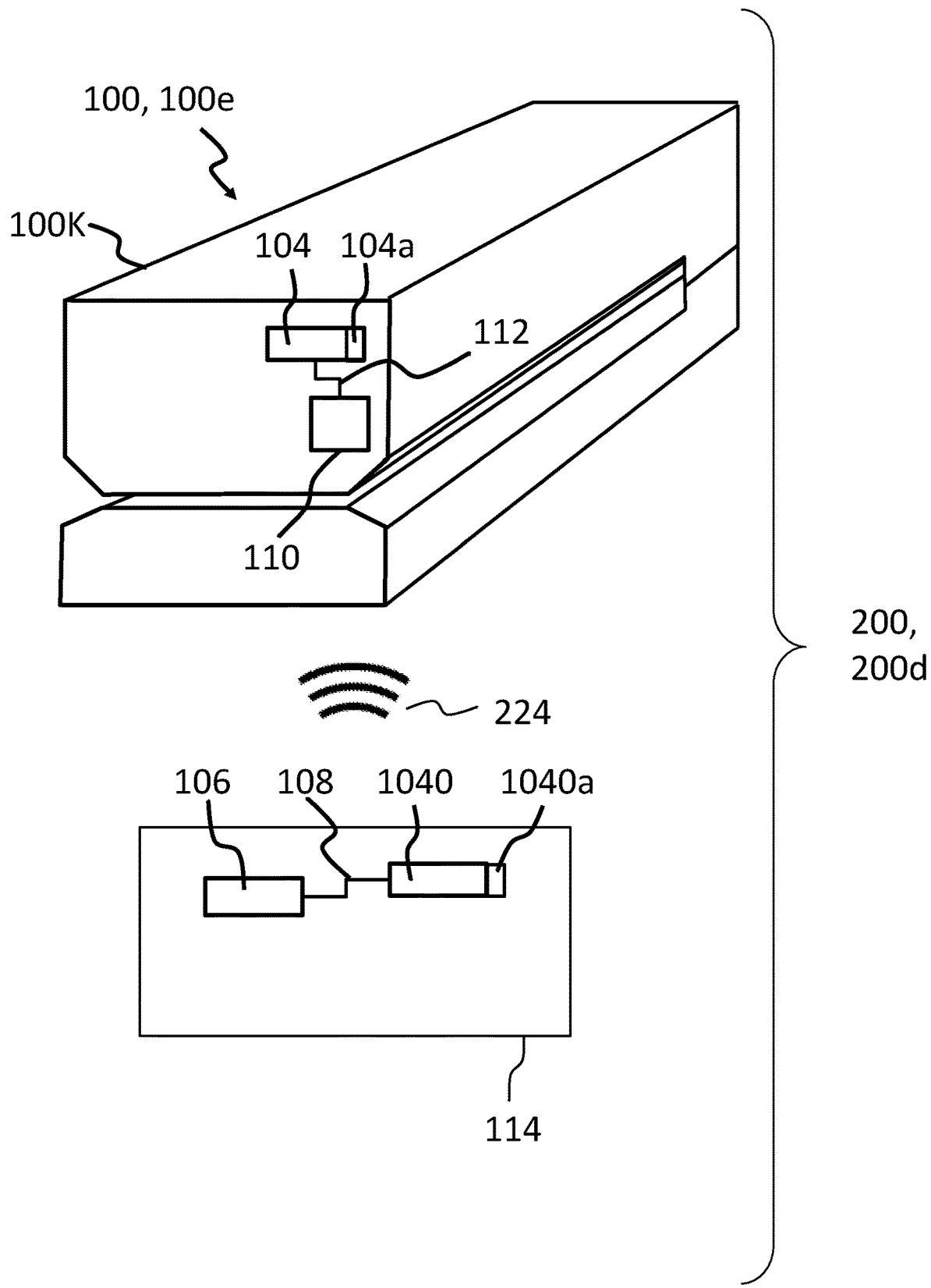
Figure 2E:
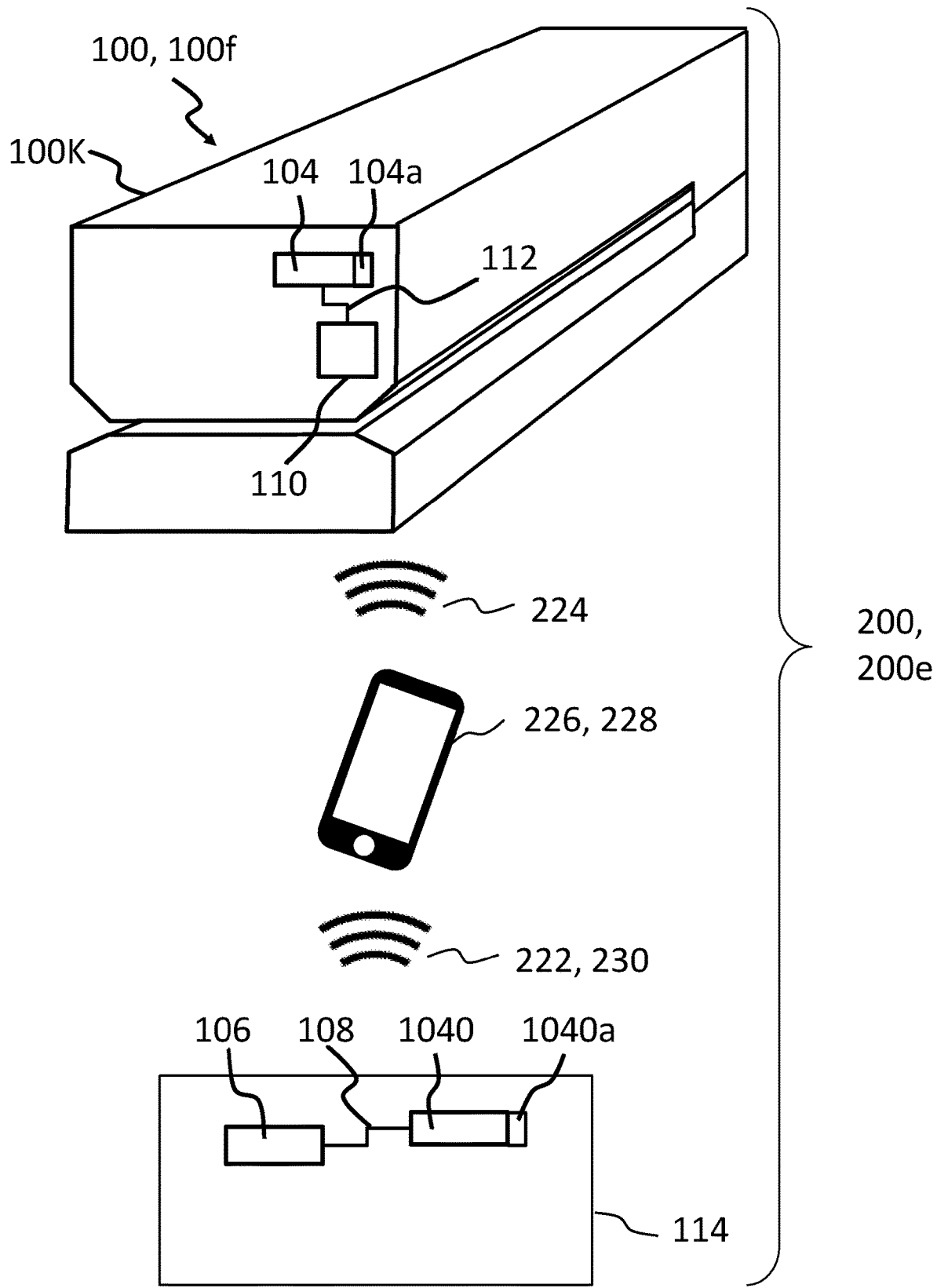
Figure 3A:
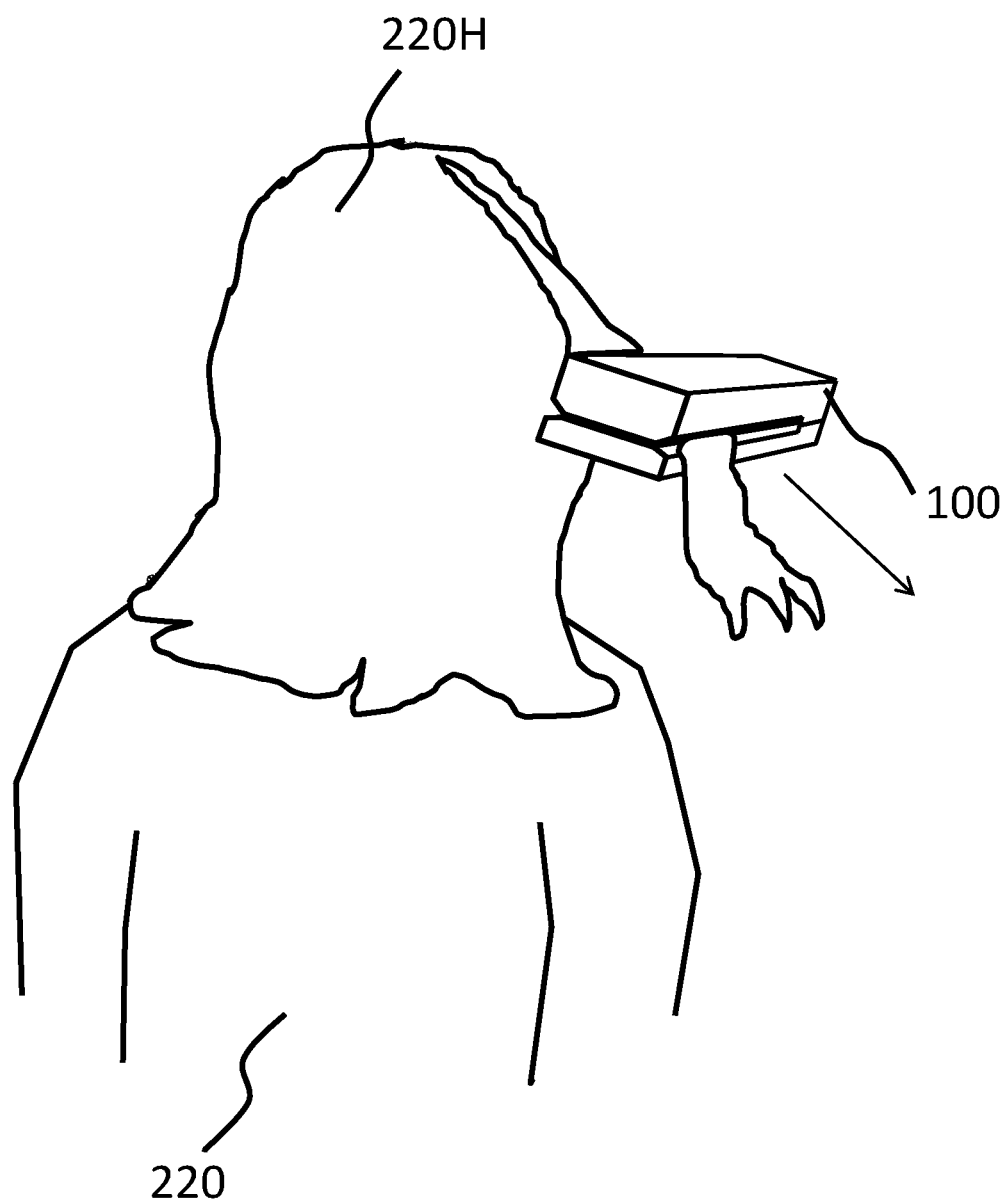
FIG. 3A is a schematic representation of an application of a hair treatment device according to various embodiments.
Figure 3B:
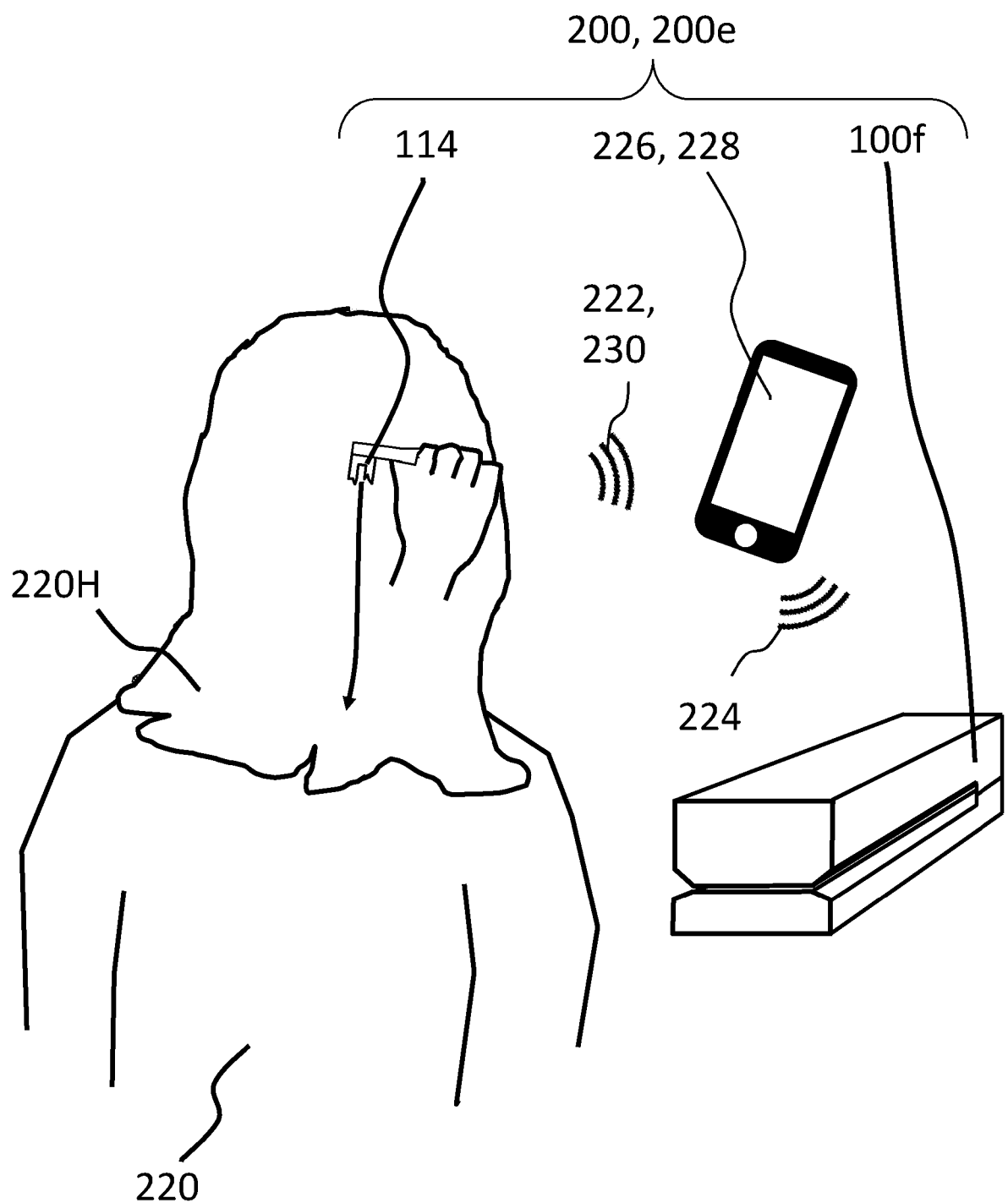
FIG. 3B is a schematic representation of an application of a hair treatment system according to various embodiments.

FIG. 1 shows a schematic representation of a hair treatment system 100 according to various embodiments, FIG. 2A to FIG. 2E each show a schematic representation of a hair treatment system 200 according to various embodiments, FIG. 3A shows a schematic representation of an application of a hair treatment system 100 according to various embodiments, and FIG. 3B a schematic representation of an application of a hair treatment system 200 according to various embodiments.

In various embodiments, a hair treatment device 100 is provided (various embodiments are identified as 100a, 100b, etc. respectively).

Although the hair treatment device 100 is shown schematically in the figures as a straightening iron, it should be understood that the hair treatment device can be of another type, for example, as described above. For example, the hair treatment device can have a curling iron, a comb, a brush, a drying hood or the like. If applicable, it should be understood that the embodiments in connection with the figures are also to apply to such types of hair treatment devices.

In various embodiments, the hair treatment device 100 can have a device body 100K.

The device body 100K can be formed of or have such a solid material, for example, plastic or metal. For example, the device body 100K can be formed of a material or have a material commonly used for a straightening iron, a comb, a brush, or the like.

In various embodiments, in particular when the hair treatment device 100, 100a has a device for semi-permanent or temporary hair forming, for example, the straightening iron, the curling iron or the drying hood, the hair treatment device 100, 100a can further have a controllable or regulatable heating device (not shown), which can, for example, be integrated into the device body 100K.

In various embodiments, the hair treatment device 100 can have at least one sensor 106 arranged in or on the device body for detecting at least one hair condition parameter, for example, a hair condition parameter as set forth above, for example, a hair moisture sensor, a hair damage sensor, a hair thickness sensor, a gray component sensor, a hair density sensor, a curl sensor, or the like.

In various embodiments, the at least one sensor 106 can be configured to detect more than one parameter, for example, the sensor 106 can have an NIR spectrometer that can be configured to detect both parameters for determining hair moisture and parameters for determining degree of hair damage, and/or the sensor 106 can have a camera, which can be configured to determine both parameters for determining the curl and parameters for determining the gray component.

In various embodiments, the sensor 106 can be incorporated in the device body 100K, for example, sealed. Thus, the hair treatment device 100 can be enabled to be insensitive to moisture and dirt. For example, the sealing can provide that the hair treatment device can be cleaned without damaging the sensor 106 or another device. For example, the sensor 106 can be molded in by injection molding of the device body 100K.

In various embodiments, for example, when the at least one sensor 106 has or includes an optical sensor, the device body 100K can be transparent between the sensor 106 and a surface of the device body 100K. In various embodiments, if it serves a purpose, the sensor 106 can be arranged in the device body 100 so as to face the hair 220H of the user 220 in a conventional arrangement of the hair on or in the hair treatment device 100 or is in contact with the hair 220H.

In various embodiments, the hair treatment device can have an electronic circuit device 104 arranged in or on the device body 100K.

The electronic circuit device 104 can, in various embodiments, be coupled to the at least one sensor 106, for example, by employing a connection 108, for receiving the detected sensor value. In the presence of a plurality of sensors 106, the circuit device 104 can have its own coupling to each of the sensors 106. The coupling can in various embodiments have or be an electrically conductive connection, a (glass) fiber connection and/or a wireless connection. The electronic circuit device 104 can be configured to receive the at least one sensor value from the at least one sensor 106.

In various embodiments, the electronic circuit device 104 can be or have a data processing device, for example, it can be equipped with a memory and a processor, for example, a microprocessor, which can be configured, for example, by programming, to receive the data from the sensor 106 and either directly control or regulate a hair treatment parameter, or to use the sensor data to provide a recommendation to the user 220.

The electronic circuit device 104 can be configured in various embodiments to determine at least one recommendation based on the received data from the sensor 106 and to provide it to the user 220.

In various embodiments, the hair treatment device can further have a controllable or regulatable actuator 110. The actuator 110 can be configured to influence a hair treatment parameter. A control or regulation of the actuator 110 can be done in various embodiments by the electronic circuit device 104. The actuator 110 can be connected to the electronic circuit device 104 by employing a connection 112 in various embodiments. The connection 112 can, in various embodiments, have or be an electrically conductive connection, a (glass) fiber connection and/or a wireless connection.

In various embodiments, the actuator 110 can have temperature control or regulation of a heatable part of the hair treatment device 100.

In various embodiments, for example, in a case where the at least one sensor 106 is used to determine a degree of hair damage, a curl, or the like, the hair treatment device 100 can be configured to control the actuator 110, for example, to set a temperature corresponding to the degree of hair damage, the curl or the like for the hair treatment, for example, a straightening process or a curling process.

In various embodiments, for example, in a case where the at least one sensor 106 is additionally used, for example, to determine a hair temperature, for example, at positions in front of and behind the heating device, the hair treatment device 100 can be configured to regulate the actuator 110, for example, a temperature for the hair treatment corresponding to the degree of hair damage, the curl or the like, for example, to adjust a straightening process or a curling process and to readjust based on the detected temperature (for example, in particular the temperature behind the heating device, that is, after the heat treatment).

In various embodiments, the hair treatment device 100 can be configured to regulate the actuator 110 based solely on temperature sensor data.

In various embodiments, for example, in the case of a straightening iron or a curling iron, the actuator 110 can be configured to be adjusted to a relatively high temperature, for example, in a range of from about 200° C. to about 230° C., if it is determined that, for example, the hair 220H of the user 220 is undamaged and/or thick, and adjusted to a relatively low temperature, for example, in a range of from about 150° C. to about 180° C., when it is determined that the hair 220H of the user 220, for example, is pre-damaged and/or thin.

In various embodiments, the user 220 can also be provided with a hair treatment recommendation, for example, in the case of the straightening or curling iron, a recommendation "to treat each strand of hair for a maximum of five seconds" or the like.

In various embodiments, the actuator 110, for example, as an alternative or in addition to the temperature control or regulation, can have a regulatable dispensing device (also referred to as a dosing device) which can be configured to dose a hair treatment agent based on the detected sensor data.

As stated above, the dispensing device can have at least one pump and/or at least one valve, which can be controllable or regulatable such that a volume or a quantity of the hair treatment agent can be dosed. In various embodiments, the dosing can be done, depending on a position of the hair treatment device 100 on the hair 220H, for example, upon determining that the hair treatment device 100 is located at the hairline, a different amount of the hair treatment agent can be delivered than with a determination that the hair treatment device 100 is located at the hair tips. For example, the hair tips can require a greater amount of hair care agent than the hairline, while it can be the other way around with a hair coloring agent.

In various embodiments, as shown in FIG. 2A, a hair treatment system 200, 200a can be provided.

The hair treatment system 200, 200a, in various embodiments, can have a hair treatment device 100, 100b, which can be similar or identical in essential parts to the hair treatment device 100a.

The hair treatment device 100, 100b can further have, in various embodiments, a data exchange device 104a, which can be configured to wirelessly transmit and receive data.

The hair treatment system 200, 200a can further have, in various embodiments, an external data processing device 226, which, for example, can be part of a smartphone, a tablet, or the like, or a cloud, for example.

As described above, the data processing device 226 can be configured to receive the detected sensor data from the data processing device 100b, to determine the control or regulation parameters and/or the at least one recommendation, and to transmit them to the hair treatment device 100b. That is, the hair treatment device 200b can be configured, as described above, to indirectly determine the control or regulation parameters and/or the at least one recommendation.

In various embodiments, as shown in FIG. 2B, a hair treatment system 200, 200b can be provided.

The hair treatment system 200, 200b, in various embodiments, can have a hair treatment device 100, 100c, which can be similar or identical in essential parts to the hair treatment device 100a and/or the hair treatment device 100b.

The data exchange device 104a of the hair treatment device 100, 100c can be configured in different embodiments to wirelessly transmit and receive data.

The hair treatment system 200, 200b can further have a display device 228 in various embodiments.

As described above, the data processing device 226 can be configured to receive the detected sensor data from the data processing device 100c, to determine the control or regulation parameters and/or the at least one recommendation, and to transmit them to the hair treatment device 100c. That is, the hair treatment device can be configured, as described above, to indirectly determine the control or regulation parameters and/or the at least one recommendation.

The display device 228 can be configured in various embodiments to receive data from the data processing device 100c, for example, a recommendation determined by the electronic circuit device 104 and/or the external data processing device 226, for example, a hair treatment recommendation and/or a recommended hair care agent.

In various embodiments, as shown in FIG. 2C, a hair treatment system 200, 200c can be provided.

The hair treatment system 200, 200c, in various embodiments, can have a hair treatment device 100, 100d, which can be similar or identical in essential parts to the hair treatment device 100a and/or the hair treatment device 100b and/or the hair treatment device 100c.

The data exchange device 104a of the hair treatment device 100, 100c can be configured in different embodiments to wirelessly transmit and receive data.

The hair treatment system 200, 200c can have a display device 228 in various embodiments.

The display device 228 can be configured in various embodiments to receive data from the data processing device 100d, for example, a recommendation determined by the electronic circuit device 104, for example, a hair treatment recommendation and/or a recommended hair care product.

In various embodiments, as shown in FIG. 2D, a hair treatment system 200, 200d can be provided.

The hair treatment system 200, 200d, in various embodiments, can have a hair treatment device 100, 100e, which can be similar or identical in essential parts to the hair treatment device 100a and/or the hair treatment device 100b and/or the hair treatment device 100c and/or the hair treatment device 100d.

The data exchange device 104a of the hair treatment device 100, 100e can be configured in different embodiments to wirelessly transmit and receive data.

In contrast to the hair treatment devices 100a to 100e, the at least one sensor 106 can not be integrated into the hair treatment device 100e but rather can be part of an external sensor device 114.

The external sensor device 114 can further have an electronic circuit device 1040 and a wireless data exchange device 1040a, which can be similar or identical to the electronic circuit device 104 and the wireless data exchange device 104a of the previous embodiments.

The electronic circuit device 1040 can be coupled to the at least one sensor 106 by employing a data connection 108, which can be similar or equal to the data connection 108 of the previous embodiments.

The external sensor device 114 can be configured to transmit to the hair treatment device 100e the detected sensor data and/or control or regulation parameters and/or recommendations determined based on the sensor data (for example, by the circuit device 1040) (shown as signal 224), for example, by the data exchange device 1040a.

The hair treatment device 100e can be configured to control or regulate the actuator 110 based on the received control and regulation parameters and/or to determine control or regulation parameters based on the received sensor data (for example, by the electronic circuit device 104) and to control or regulate the actuator 110 based on the determined control or regulation parameters.

In various embodiments, as shown in FIG. 2E, a hair treatment system 200, 200e can be provided.

The hair treatment system 200, 200e can, in various embodiments, have a hair treatment device 100, 100f which can be similar or identical in essential parts to the hair treatment device 100a and/or the hair treatment device 100b and/or the hair treatment device 100c and/or the hair treatment device 100d and/or the hair treatment device 100e.

The data exchange device 104a of the hair treatment device 100, 100e can be configured in different embodiments to wirelessly transmit and receive data.

In contrast to the hair treatment system 200d, the hair treatment device 100f and the external sensor device 114 can be configured not to exchange their data directly with each other, but rather by employing a combined data processing and display device 226, 228 (for example, a smartphone, a tablet, a laptop, or the like). Expressed otherwise, the combined data processing and display device 226, 228 can act as the heart of the hair treatment system 200e. For example, an app or a program can be installed on the combined data processing and display device 226, 228, which app or program can be configured to manage the detection of the sensor data and the control/regulation of the hair treatment parameters, possibly, for example, alternatively or in addition to the electronic circuit device 104 and/or the electronic circuit device 1040, to itself determine the control or regulation parameters and/or the recommendation and/or, possibly, alternatively or in addition to the hair treatment device 100f, to provide the recommendation, for example, by the display device 228 or for example, by a speaker.

In various embodiments, the combined data processing and display device 226, 228 can further be configured to provide the sensor data to a (further) external data processing device 226, for example, a cloud, and to transmit from the (further) external data processing device 226 the control or regulation parameters and/or the recommendation of the hair treatment device 100f received therefrom and/or to provide the recommendation.

In various embodiments, to determine a hair condition, for example, a degree of hair damage or the like, a database can be used, as described above, in which the sensor data or possibly combinations of sensor data, the hair conditions (for example, degrees of hair damage) can be assigned. The database can have been previously created by experiments, and/or can be continually created or supplemented by user data, for example, when using a cloud.

In various embodiments, the database can further provide a product recommendation based on the hair condition, for example, degree of hair damage.

As shown in the following table, for example, at least one product recommendation (or also a styling or other hair treatment recommendation) can be assigned to the degree of hair damage in the database.

| Degree of hair damage | Product recommendation |
| --- | --- |
| very low | Product having very little care content |
| low | Product having little care content |
| medium | Product having medium care content |
| strong | Product having high care content |
| very strong | Product having very high care content |

The measured sensor values can, as described above, either be evaluated directly in the hair treatment device 100, for example, by the electronic circuit device 104, or indirectly evaluated by being transmitted to an external data processing device 226 to be evaluated there, for example, as described above. In this case, the sensor data or parts of the sensor data can be evaluated in various embodiments by a comparison with (for example, empirically obtained) database entries.

In various embodiments, a determined hair condition (for example, degree of hair damage) can be included in determining a recommendation, for example, a product or treatment recommendation.

In various embodiments, the determined hair treatment agent, for example, hair care agent, can be applied to the hair by the hair treatment device or the hair treatment system, wherein control or regulation parameters for dosing the hair treatment agent by the electronic circuit device 104, the electronic circuit device 1040 and/or the external data processing device 226 and/or the further external data processing device can be provided.

FIG. 3A shows a schematic representation of an application of a hair treatment system 100 according to various embodiments, and FIG. 3B shows a schematic representation of an application of a hair treatment system 200, 200e according to various embodiments.

As shown in FIG. 3A, the hair treatment device 100a can be used in the way usual for a hair treatment device for the hair treatment. A straightening iron is shown, in which the hairs 220H are pinched in strands and which is typically moved in the arrow direction, that is, in the direction from the hairline towards the hair tips. Analogously, for example, when using a curling iron as a hair treatment device, the hair is wound up by strands on the hair treatment device 100, the hair is combed through by strands when using a comb as a hair treatment device, etc.

In contrast to the conventional hair treatment device, the hair treatment device 100 according to various embodiments can be configured, during the hair treatment, for example, as described above, to detect at least one sensor value by at least one sensor 106 and to control or regulate at least one hair treatment parameter and/or provide at least one recommendation.

As shown in FIG. 3B, the hair treatment system 200 can be used for a hair treatment. As described above, an external sensor device 114 can be used to determine at least one hair condition parameter, for example, a degree of hair damage or the like. For this purpose, the external sensor device 114 can be brought into optical and/or physical contact with the hair 220H of the user 220.

As described above, the at least one sensor value and/or a hair condition parameter determined therefrom and/or a control or regulation parameter can be transmitted to the combined data processing/display device 226, 228 (shown as signal 222, 230) and the at least one sensor value and/or or a hair condition parameter determined therefrom and/or a control or regulation parameter can be transmitted to the hair treatment device 100f, for example, for controlling and/or regulating the at least one actuator 110 and/or for displaying the at least one recommendation.

Shown here is a transmission of the at least one sensor value and/or a hair condition parameter determined therefrom and/or a control or regulation parameter to the hair treatment device 100f before using the hair treatment device 100f. In various embodiments, the transmission can also be made simultaneously with the use.

In various embodiments, the other hair treatment devices and hair treatment systems described above can be used analogously similarly as described herein by way of example for each of the hair treatment devices and each of the hair treatment systems.

FIG. 4 shows a flowchart 400 of a method for the cosmetic treatment of hair of a user according to various embodiments.

In various embodiments, the method of cosmetically treating hair of a user can have a detecting of a hair condition parameter by at least one sensor during a treatment and/or before a treatment of hair by a hair treatment device or by a hair treatment system according to various embodiments (in 410) and a controlling of at least one hair treatment parameter and/or dosing of at least one hair treatment agent and/or recommending at least one hair treatment based on the at least one hair condition parameter (in 420).

Programming, for example, software, can be used in various embodiments for the determinations described above. In this case, any software that provides a functionality described above can be used. In various embodiments, for example, in a case that a smartphone, a tablet or the like is used to carry out the method for the cosmetic treatment of hair of a user according to various embodiments, the software can be provided as an app.

In various embodiments, the circuit device integrated into the hair treatment device and/or an external data processing device, for example, a smartphone, a tablet, a laptop, a smart mirror, a smartwatch, an iPad, or the like, can be suitable in order to be used when carrying out the method of providing a hair condition information item, for example, in determination operations, for example, by comparing with a database/reference values or the like. In various embodiments, the programming/software does not need to be provided on the smartphone, tablet, laptop, etc. For example, it can be sufficient when the circuit device integrated into the hair treatment device and/or the smartphone or the like is connected through the Internet, by WLAN or in another common way to a (for example, a further) external data processing device, for example, a computer, for example, a cloud. In such a case, the calculations can be carried out, for example, by the (further) external data processing device, for example, by the computer, and the result can be provided to the smartphone/tablet or the like and/or the internal circuit device.

Further advantageous embodiments of the method are apparent from the description of the device and vice versa.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A hair treatment device, comprising:
a device body;
at least one sensor arranged in or on the device body, the at least one sensor configured to detect a plurality of hair condition parameters and a position of the device body; and
an electronic circuit device arranged in or on the device body,
the electronic circuit device coupled to receive the detected plurality of hair condition parameters and the position of the device body from the at least one sensor and to determine, from the detected plurality of hair condition parameters, a degree of hair damage,
wherein the electronic circuit device is configured to control at least one hair treatment parameter based on the determined degree of hair damage and to dose at least one hair treatment agent based on the determined degree of hair damage and dependent on the position of the device body, and
wherein the at least one sensor further includes at least one of a microphone or a tensile force gauge.

2. The hair treatment device according to claim 1, wherein the hair treatment device has a straightening iron.

3. The hair treatment device according to claim 1, wherein the controlled hair treatment parameter is a temperature of the hair treatment device.

4. The hair treatment device according to claim 1, wherein the at least one sensor is arranged to be brought into contact with hair of a user during the detection of the plurality of hair condition parameters.

5. The hair treatment device according to claim 1, wherein the electronic circuit is further configured to provide a hair treatment recommendation, where the hair treatment recommendation is at least one of a hair care product recommendation, a hair styling product recommendation, and a hair treatment recommendation.

6. The hair treatment device according to claim 1, wherein the at least one sensor is arranged sealed in the device body.

7. The hair treatment device according to claim 1, wherein the electronic circuit device has a wireless data exchange device.

8. The hair treatment device according to claim 1, wherein the at least one sensor further includes at least one of:
a camera for recording a digital image of the hair;
a temperature sensor;
a moisture sensor; and
a color sensor.

9. A method of cosmetically treating hair of a user, the method comprising the steps of:
during a treatment and/or before a treatment of the hair by a hair treatment device according to claim 1, detecting the plurality of hair condition parameters and the position of the hair treatment device with the at least one sensor; and
dosing the at least one hair treatment agent based on the determined degree of hair damage and dependent on the position of the hair treatment device.

10. The method according to claim 9,
wherein the hair treatment device has a straightening iron.

11. The method of claim 9, further comprising the steps of:
transmitting the detected plurality of hair condition parameters to an external data processing device; and
receiving the information provided by the external data processing device,
wherein determining the hair treatment agent dosing is done based on the plurality of hair condition parameters by the external data processing device.

12. A hair treatment system, comprising:
a hair treatment device including:
a device body;
at least one sensor arranged in or on the device body, the at least one sensor configured to detect a plurality of hair condition parameters and a position of the device body; and
an electronic circuit device arranged in or on the device body, wherein the electronic circuit device is coupled to receive the detected plurality of hair condition parameters and the position of the device body from the at least one sensor and the electronic circuit device is configured to determine, from the detected plurality of hair condition parameters, a degree of hair damage, and to (i) control at least one hair treatment parameter and (ii) dose at least one hair treatment agent based on the determined degree of hair damage and dependent on the position of the device body, wherein the electronic circuit device has a wireless data exchange device; and
a display device in operable communication with the hair treatment device,
wherein the hair treatment device is configured to transmit to the display device at least the hair condition information item, and
wherein the at least one sensor further includes at least one of a microphone or a tensile force gauge.

13. A method of cosmetically treating hair of a user, the method comprising the steps of:
during treatment and/or before a treatment of the hair by a hair treatment system according to claim 12, detecting the plurality of hair condition parameters and the position of the hair treatment device by the at least one sensor; and
controlling the at least one hair treatment parameter and dosing the at least one hair treatment agent determined degree of hair damage and dependent on the position of the hair treatment device.

14. A hair treatment system, comprising:
a device body;
at least one sensor arranged in or on the device body, the at least one sensor configured to detect a hair condition parameter and a position of the device body;
an electronic circuit device having a wireless data exchange device arranged in or on the device body; and
a data processing device;

wherein the electronic circuit device is coupled to receive the detected hair condition parameter and the position of the device body from the at least one sensor, wherein the electronic circuit device is configured to transmit the received hair condition parameter to the data processing device by the wireless data exchange device, wherein the data processing device is configured, based on the received detected hair condition parameter, to determine a dosage of a hair treatment agent from a tank and to transmit to the electronic circuit device or a further electronic circuit device arranged in a treatment device by the wireless data exchange device, and wherein the electronic circuit device or the further electronic circuit device is further configured to dose the at least one hair treatment agent dependent on the position of the device body, and wherein the at least one sensor further includes at least one of a microphone or a tensile force gauge.

15. The hair treatment system according to claim 14, wherein the at least one sensor further includes one or more of a camera for recording a digital image of the hair, a temperature sensor, a moisture sensor, and a color sensor.

\* \* \* \* \*